US008759093B2

(12) United States Patent
France et al.

(10) Patent No.: US 8,759,093 B2
(45) Date of Patent: *Jun. 24, 2014

(54) METHOD FOR DETERMINING THE SELECTIVITY OF A PRE-SYNAPTIC NEUROMUSCULAR BLOCKING SUBSTANCE

(75) Inventors: Richard France, Nottingham (GB); Robin Quirk, Nottingham (GB); Lisa Riccalton-Banks, Nottingham (GB); Andrew Martin Pickett, Berkshire (GB)

(73) Assignee: Ipsen Developments Limited, Berkshire (GB)

( * ) Notice: Subject to any disclaimer, the term of this patent is extended or adjusted under 35 U.S.C. 154(b) by 1736 days.

This patent is subject to a terminal disclaimer.

(21) Appl. No.: 11/659,445

(22) PCT Filed: Aug. 2, 2005

(86) PCT No.: PCT/GB2005/003032
§ 371 (c)(1),
(2), (4) Date: Jan. 22, 2008

(87) PCT Pub. No.: WO2006/013354
PCT Pub. Date: Feb. 9, 2006

(65) Prior Publication Data
US 2008/0213820 A1 Sep. 4, 2008

(30) Foreign Application Priority Data
Aug. 4, 2004 (GB) .................................. 0417366.2

(51) Int. Cl.
*C12N 5/07* (2010.01)
*C12N 5/071* (2010.01)
*G01N 33/50* (2006.01)

(52) U.S. Cl.
CPC .......... *C12N 5/0661* (2013.01); *G01N 33/5082* (2013.01)
USPC ........................................ 435/347; 435/7.21

(58) Field of Classification Search
CPC ................................................. G01N 33/5082
USPC ....................................................... 435/7.21
See application file for complete search history.

(56) References Cited

FOREIGN PATENT DOCUMENTS

GB    2398636 A      8/2004
WO    WO2004/074838  9/2004

OTHER PUBLICATIONS

Smith et al. "Effect of stimulation intensity and botulinum toxin isoform on rat bladder strip contractions", Brain Research Bulletin, 2003, 61:165-171.*
Vizi et al. "Side effects of nondepolarizing muscle relaxants: relationship to their antinicotinic and antimuscarinic actions", Pharmacol. Ther. 1997, 73(2):75-89.*
Göschel et al, Experimental Neurology 147, 1997, pp. 96-102, *Botulinum* A Toxin Therapy: Neutralizing and Nonneutralizing . . . .
Sheridan et al, J. Appl. Toxicol. 19, 1999, pp. S29-S33, Comparison of In Vivo and In Vitro Mouse Bioassays for . . . .
Foldes, Life Sciences, vol. 28, 1981, pp. 1585-1590, The Significance of Physiological [$Ca^{2+}$] and [$Mg^{2+}$] for in vitro . . . .
Healy et al, Br. J. Anaesth. 54, 1982, pp. 1307-1311, In Vitro Comparison Between the Neuromuscular and Ganglion Blocking . . . .
Birmingham et al, Br. J. Pharmac. 70, 1980, pp. 501-506, A Comparison of the Skeletal Neuromuscular and Autonomic . . . .
James et al, Am. J. Physiol. Gastrointest Liver Physiol. 285, 2003, pp. G291-G297, Inhibitory effects of *botulinum* toxin . . . .
Pearce et al, Toxicom, vol. 35, No. 9, 1997, pp. 1373-1412, Pharmacologic Characterization of *Botulinum* Toxin for Basic . . . .
Chang et al, Naunyn-Schmiedberg's Arch. Pharmacol. 282, 1974, pp. 129-142, Comparison of the Presynaptic Actions of . . . .
Longhurst et al, Jour. of Pharm. & Toxicol. Methods 45, 2001, pp. 91-108, Pharmacological Techniques for the In Vitro . . . .
Wohlfarth et al, Naunyn-Schmiedeberg's Arch Pharmacol. 355, 1997 pp. 335-340, *Boluinum* A toxins: units versus units.

* cited by examiner

*Primary Examiner* — Bin Shen
(74) *Attorney, Agent, or Firm* — Jacobson Holman, PLLC.

(57) ABSTRACT

The present invention relates to a method for determining the selectivity of a pre-synaptic neuromuscular blocking substance for striated muscle or smooth muscle. The method comprises measuring the effect induced by a pre-determined quantity of pre-synaptic neuromuscular blocking substance upon electrically stimulating striated muscle tissue, measuring the effect induced by a pre-determined quantity of a pre-synaptic neuromuscular blocking substance upon electrically stimulating smooth muscle tissue, and calculating a quotient of the results obtained in order to determine the selectivity of the pre-synaptic neuromuscular blocking substance for striated muscle or for smooth muscle.

14 Claims, 8 Drawing Sheets

METHOD FOR DETERMINING THE SELECTIVITY OF A PRE-SYNAPTIC NEUROMUSCULAR BLOCKING SUBSTANCE

This is a national stage of PCT/GB2005/003032 filed 2 Aug. 2005 and published in English.

The invention relates to a method for determining the selectivity of a pre-synaptic neuromuscular blocking substance.

The determination of the quantity of pre-synaptic neuromuscular blocking substance contained in a sample is generally made through the measurement of the lethal dose $LD_{50}$ for this substance in mice or rats. This method is in particular used presently for the determination of the quantity of active botulinum toxin. Such $LD_{50}$ methods are synonym of a large number of animals killed.

While this method allows the quantification of the pre-synaptic neuromuscular blocking substance present in a sample, it does not allow to determine the selectivity of said substance between striated and smooth muscles. Knowing this selectivity would however constitute a great advantage when carrying out research in this field: indeed, a pre-synaptic neuromuscular blocking substance selective for smooth muscles would allow to treat diseases of smooth muscles without secondary effects on striated muscles (and vice versa).

The present invention offers a process for determining the selectivity of a pre-synaptic neuromuscular blocking substance. This process uses an ex vivo method which spares the life of a significant number of animals compared to the usual $LD_{50}$ methods, which method is described in a PCT patent application by the same Applicant, i.e. PCT application No. PCT/GB2004/000697.

PCT application No. PCT/GB2004/000697 discloses a method for determining the quantity of a pre-synaptic neuromuscular blocking substance in a sample which comprises the following steps:

(i) determining the minimum voltage $V_m$ needed to induce the contraction of muscle tissue, said muscle tissue being connected to an electrical stimulator through a motor nerve;
(ii) adding the sample containing the pre-synaptic neuromuscular blocking substance;
(iii) electrically stimulating, at a voltage at least equal to $V_m$, the muscle tissue at certain time intervals;
(iv) comparing the effect induced by the sample to the effect induced by a reference substance and thereby determining the quantity of the pre-synaptic neuromuscular blocking substance in the sample.

In PCT application No. PCT/GB2004/000697, there is however no mention that the muscle tissue could be a smooth muscle and a rib (striated) muscle is used in each example.

A first aspect of the invention relates to a method for determining the quantity of a pre-synaptic neuromuscular blocking substance in a sample which comprises the following steps:

(i) determining the minimum voltage $V_{msm}$ needed to induce the contraction of a smooth muscle tissue, said smooth muscle tissue being linked to an electrical stimulator through an electrically conducting liquid;
(ii) adding the sample containing the pre-synaptic neuromuscular blocking substance;
(iii) electrically stimulating, at a voltage at least equal to $V_{msm}$, the smooth muscle tissue at certain time intervals;
(iv) comparing the effect induced by the sample to the effect induced by a reference substance and thereby determining the quantity of the pre-synaptic neuromuscular blocking substance in the sample.

The instant invention also offers a method for determining the selectivity of a pre-synaptic neuromuscular blocking substance comprising the following steps:

(a) determining the minimum voltage $V_{mst}$ needed to induce the contraction of a striated muscle tissue, said striated muscle tissue being connected to an electrical stimulator through a motor nerve;
(b) adding to the system of step (a) a pre-determined quantity of a pre-synaptic neuromuscular blocking substance;
(c) electrically stimulating, at a voltage at least equal to $V_{mst}$, the muscle tissue at certain time intervals;
(d) measuring the effect induced by the pre-determined quantity of a pre-synaptic neuromuscular blocking substance on the striated muscle tissue;
(e) determining the minimum voltage $V_{msm}$ needed to induce the contraction of a smooth muscle tissue, said smooth muscle tissue being linked to an electrical stimulator through an electrically conducting liquid;
(f) adding to the system of step (e) the same pre-determined quantity of the same pre-synaptic neuromuscular blocking substance as for step (b);
(g) electrically stimulating, at a voltage at least equal to $V_{msm}$, the muscle tissue at certain time intervals;
(h) measuring the effect induced by said pre-determined quantity of the pre-synaptic neuromuscular blocking substance on the smooth muscle tissue;
(i) calculating the quotient of the result obtained after step (h) by the result obtained after step (d), or, conversely, the quotient of the result obtained after step (d) by the result obtained after step (h).

The quotient of the result obtained after step (h) by the result obtained after step (d) indicates the selectivity of the pre-synaptic neuromuscular blocking substance tested for smooth muscles compared to striated muscles; the higher above 1 this quotient is, the more selective for smooth muscles the pre-synaptic neuromuscular blocking substance is.

The quotient of the result obtained after step (d) by the result obtained after step (h) indicates the selectivity of the pre-synaptic neuromuscular blocking substance tested for striated muscles compared to smooth muscles; the higher above 1 this quotient is, the more selective for striated muscles the pre-synaptic neuromuscular blocking substance is.

Preferably, the striated muscle and the smooth muscle tissues will be taken from the same animal species, and more preferably from the same animal.

By pre-synaptic neuromuscular blocking substance should be understood in the present application a substance that prevents and/or inhibits transmission of the chemical messages and signals involved in pre-synaptic neuromuscular activity. Examples of pre-synaptic neuromuscular blocking substances are substances that inhibit acetylcholine (ACH) synthesis or release; those include notably biological toxins (such as botulinum neurotoxins and bungarotoxins) and chemicals (such as hemicholinium or triethylcholine which inhibit ACH synthesis, aminoglycoside antibiotics which inhibit ACH release or tubocurarine and similar compounds). Preferred pre-synaptic neuromuscular blocking substances according to this invention will be botulinum neurotoxins and bungarotoxins (α-bungarotoxin being preferred among the bungarotoxins).

By botulinum neurotoxins (or botulinum toxins) is meant in the present application botulinum neurotoxin complexes (whether of type A, B, C, D, E, F or G) as well as high purity botulinum neurotoxins (whether of type A, B, C, D, E, F or G). Botulinum toxin type A includes all types of botulinum toxin type A, including A1, A2 and A3.

By botulinum neurotoxin complex (whether of type A, B, C, D, E, F or G) should be understood in the present application a botulinum neurotoxin (whether of type A, B, C, D, E, F or G) associated with at least another non-toxic protein.

By high purity botulinum neurotoxin (whether of type A, B, C, D, E, F or G) is meant, in the present application, botulinum neurotoxin (whether of type A, B, C, D, E, F or G) outside from complexes including at least another protein. In other words, a high purity botulinum neurotoxin (type A, B, C, D, E, F or G) does not contain significant quantities of any other *Clostridium* spp derived protein than botulinum neurotoxin (type A, B, C, D, E, F or G).

By muscle tissue is meant, in the present application, a muscular fibre sample comprising one or more muscle fibres. If not further specified, a muscle tissue may be, in the present application, a striated muscle tissue or a smooth muscle tissue.

Preferably, the muscle tissue, whether striated or smooth, is immersed in a buffer, such as a physiological buffer. The buffer may comprise an energy source. The energy source may be an ATP energy source, for example one or more of the following: ATP, a sugar such as glucose and/or creatine (including creatine phosphate), a fatty acid, an amino acid, glycogen and pyruvic acid. The buffer may be oxygenated, particularly for longer assays. In a preferred embodiment, the buffer is an oxygenated physiological buffer containing glucose.

The buffer in which the striated muscle tissue is immersed will preferably contain at least 10 mM of glucose (e.g. 11 mM). Preferably also, the buffer will be saturated in oxygen (e.g. by bubbling oxygen or a 95/5 $O_2/CO_2$ mixture through the buffer). Furthermore, the buffer will preferably contain from 100 to 200 mM of NaCl, from 1 to 5 mM of KCl, from 10 to 15 mM $NaHCO_3$, from 0.5 to 2 mM of $MgCl_2$ and from 1 to 5 mM of $CaCl_2$. The pH of the buffer will preferably be about 7.4.

The buffer in which the smooth muscle tissue is immersed will preferably be a Krebs-Henseleit type buffer. By Krebs-Henseleit type buffer should be understood a buffer that contains D-glucose (preferably at least 1 g/l and more preferably about 2.1 g/l), magnesium sulphate (preferably at least 0.1 g/l and more preferably about 0.29 g/l), monobasic potassium phosphate $KH_2PO_4$ (preferably at least 0.1 g/l and more preferably about 0.16 g/l), potassium chloride (preferably at least 0.25 g/l and more preferably about 0.35 g/l), sodium chloride (preferably at least 5 g/l and more preferably about 6.9 g/l), calcium chloride (preferably at least 0.25 g/l and more preferably about 0.282 g/l) and sodium bicarbonate $NaHCO_3$ (preferably at least 1.5 g/l and more preferably about 2.1 g/l).

An alternative preferred buffer for immersing the smooth muscle tissue is a standard type Krebs buffer. By standard Krebs type buffer should be understood a buffer that contains D-glucose (preferably at least 10 mmol/l and more preferably about 11.5 mmol/l), sodium chloride (preferably at least 100 mmol/l and more preferably about 113 mmol/l), potassium chloride (preferably at least 2.5 mmol/l and more preferably about 4.7 mmol/l), calcium chloride (preferably at least 1 mmol/l and more preferably about 1.25 mmol/l), magnesium sulphate (preferably at least 1 mmol/l and more preferably about 1.2 mmol/l), sodium bicarbonate $NaHCO_3$ (preferably at least 20 mmol/l and more preferably about 25 mmol/l) and monobasic potassium phosphate $KH_2PO_4$ (preferably at least 1 mmol/l and more preferably about 1.2 mmol/l).

Preferably, the abovementioned methods will be such that the electrical stimulation of step (iii) of the method for determining the quantity of a pre-synaptic neuromuscular blocking substance in a sample or step (c) or step (g) of the method for determining the selectivity of a pre-synaptic neuromuscular blocking substance is carried out at a voltage at least equal to the supramaximal voltage $V_{SM}$. By supramaximal voltage is understood the minimum voltage to get the maximum twitch response of the muscle tissue.

According to a first variant of the invention (hereafter variant A), the effect induced used for the comparison of step (iv) of the method for determining the quantity of a pre-synaptic neuromuscular blocking substance in a sample or the measurement of step (d) or step (h) of the method for determining the selectivity of a pre-synaptic neuromuscular blocking substance is the time to paralysis of the muscle tissue (also named "lifetime" in this application). According to subvariants, the time to paralysis may be determined based (variant A1) on the muscle contraction distance (paralysis being achieved once the contraction distance is equal to zero) or (variant A2) on the muscle twitch frequency (paralysis being achieved once the twitch frequency is equal to zero).

According to another variant of the invention (hereafter variant B), the effect induced used for the comparison of step (iv) of the method for determining the quantity of a pre-synaptic neuromuscular blocking substance in a sample or the measurement of step (d) or step (h) of the method for determining the selectivity of a pre-synaptic neuromuscular blocking substance is the variation in the contraction rate of the muscle tissue.

According to another variant of the invention (hereafter variant C), the effect induced used for the comparison of step (iv) of the method for determining the quantity of a pre-synaptic neuromuscular blocking substance in a sample or the measurement of step (d) or step (h) of the method for determining the selectivity of a pre-synaptic neuromuscular blocking substance is the variation in the contraction distance of the muscle tissue.

According to still another variant of the invention (hereafter variant D), the effect induced used for the comparison of step (iv) of the method for determining the quantity of a pre-synaptic neuromuscular blocking substance in a sample or the measurement of step (d) or step (h) of the method for determining the selectivity of a pre-synaptic neuromuscular blocking substance is the variation in the force of contraction of the muscle tissue.

According to a further variant of the invention (hereafter variant E), the effect induced used for the comparison of step (iv) of the method for determining the quantity of a pre-synaptic neuromuscular blocking substance in a sample or the measurement of step (d) or step (h) of the method for determining the selectivity of a pre-synaptic neuromuscular blocking substance is the variation in the end plate potential or the miniature end plate potential of the muscle tissue.

Preferred methods for measuring toxin effect use the force (or voltage) vs time curve and measurement via either:
i. the time for the muscle contraction force to reach a certain percentage (for example 75% or 50%) of the maximum peak (contraction) height,
ii. the area under the curve (which may be adjusted for maximum peak height, or
iii. comparison of the slope of part or all of the curve (which may be related to the maximum peak height of the curve).

Combinations of the variants A (including its subvariants), B, C, D and E may be used by the person skilled in the art in order to achieve an improvement in the accuracy of the results obtained. In particular, the person skilled in the art may think of combining subvariant A1 and subvariant A2.

Preferably, the pre-synaptic neuromuscular blocking substance will be a botulinum neurotoxin. In particular, the botulinum neurotoxin may be selected from botulinum neurotoxin type A, botulinum neurotoxin type B and botulinum neurotoxin type F. More preferably, the botulinum neurotoxin will be selected from botulinum neurotoxin type A and botulinum neurotoxin type B. In a particularly preferred manner, the botulinum neurotoxin will be botulinum neurotoxin type A, notably a botulinum neurotoxin type A complex (like the active principles of the commercial products Dysport® or Botox®).

In a general manner, the method for determining the quantity of a pre-synaptic neuromuscular blocking substance in a sample will be more sensitive at lower concentrations (for example 0 to 100 $LD_{50}$ units/ml, and preferably 0 to 50 or 0 to 10 $LD_{50}$ units/ml) while it may not work when high concentrations in pre-synaptic neuromuscular blocking substances are present in the sample (the muscle tissue remaining paralysed despite electrical stimulation). As a consequence, the sample to be tested will preferably be prepared in at least two or three dilutions (for example, non diluted, diluted 10 times and diluted 100 times) on which the invention method will be carried out; in that way, higher concentrations in pre-synaptic neuromuscular blocking substances can also be determined. However, the sensitivity of the method described previously can be improved as mentioned below.

According to a preferred execution mode of the invention, the striated muscle tissue will be constituted by a piece of rib muscle obtained from a mouse or a rat. Preferably, this piece will have a dimension of at least 2 mm by 10 mm. The striated muscle tissue could for example have a size corresponding to a 2-rib section of the rib muscle.

According to a preferred execution mode of the invention, the smooth muscle tissue will be constituted by a piece of bladder of a pig or a rat. Preferably, this piece will have a dimension of at least 2 mm by 10 mm. Other common species sources include guinea pig and rabbit. Other tissue sources that may be used include anal canal/sphincter muscle, iris spincter and associated dilator muscles, and intestinal tissue, preferably duodenal and possibly Spincter of Oddi.

According to a further preferred execution mode of the invention, each electrical stimulation will always consist in applying a voltage $V_S$ which is at least equal to the minimum voltage $V_{mst}$ or $V_{msm}$ that is needed to induce the contraction of the muscle tissue, $V_S$ being besides inferior or equal to a voltage which is slightly above $V_{mst}$ or $V_{msm}$. The "voltage that is slightly above $V_{mst}$ or $V_{msm}$" may be $V_{mst}$ or $V_{msm}$ plus 3 Volts, $V_{mst}$ or $V_{msm}$ plus 2 Volts or $V_{mst}$ or $V_{msm}$ plus 1.5 Volt. For example, the stimulation voltage applied may be chosen as $V_{mst}$ or $V_{msm}$ plus 1 Volt.

Further possible features of the invention include the use of a video camera combined with a video recorder. The films produced can then be analysed and the effect of the pre-synaptic neuromuscular blocking substance precisely evaluated. The quantity of pre-synaptic neuromuscular blocking substance present in the sample can then be derived from the effect observed for the sample compared to that observed for the reference.

Alternatively, for the variant D stated above, the force displacement transducer used to measure the force of contraction of the muscle tissue can be associated with an automatic real-time electronic data capture system.

In order to reduce result variability, the electrical stimulator will send at specified time intervals the chosen voltage $V_S$, which each time will bring about a certain effect. Using the mean effect observed in these conditions will allow to make a more accurate determination of the quantity of pre-synaptic neuromuscular blocking substance present in the sample.

A way of increasing sensitivity for the method consists in carrying out the method over a longer period of time, allowing more data to be captured (for example over a period of at least 5, 10 or 30 minutes and of up to 1, 2, 4, 8, 12, 24, 48, 72 hours or even more). For example, for variant D of the method, the method could be carried out until a reduction in a certain proportion of the force of contraction of the muscle tissue is measured (e.g. a reduction of 10, 20, 25, 30, 40, 50, 60, 70, 75, 80 or 90%).

In order to carry out this preferred execution mode, the life span of the muscle tissue needs to be extended compared to the more general method explained earlier.

In one particular approach aimed at extending said life span, oxygen and glucose (or other ATP source) are provided in a regular manner to the muscle tissue.

One way to achieve this is to exchange at regular intervals an oxygenated physiological buffer bath containing glucose (or other ATP source) with a new one in order to have the consumed oxygen and glucose (or other ATP source) replaced (wherein said intervals are preferably not less than 1 minute and not more than 24 hours, e.g. every 1, 2, 5, 10, 15 or 60 minutes). Another way consists in using a bath wherein oxygen is constantly bubbled, which allows to keep the oxygen concentration of the bath constant; additionally, glucose (or other ATP source) may be added at regular intervals to replace the glucose (or other ATP source) consumed by the muscle tissue. However this may be unnecessary as it has been observed that glucose consumption by the tissue is usually minimal over the time course of the experiment Alternatively, a flow-through bath system can be used, which has the advantage of keeping constant glucose (or other ATP source) and optionally oxygen levels. In this system, the oxygenated physiological buffer containing glucose (or other ATP source) is pumped in at one end of the vessel in which the muscle tissue is immersed and pumped out at the other end.

Other means to extend the life span of the muscle tissue include the use of a train pulse stimulation which reduces the sample's fatigue. By train pulse stimulation is meant stimulations lasting a time $t_S$ separated from each other by periods lasting a time $t_P$ during which no stimulation is exerted. The time $t_S$ will preferably be from. 50 µs to 500 ms, more preferably from 100 µs to 250 ms and even more preferably from 100 µs to 1 ms (e.g. 200 µs or about 200 µs); the time $t_P$ will preferably be from 0.1 to 10 s, and more preferably from 0.5 and 2 s (e.g. 1 s or about 1 s); the ratio $t_S/t_P$ will preferably be from 1:2 to 1:50 000, more preferably from 1:5 to 1:20 000 and even more preferably from 1:500 to 1:10 000 (e.g. about 1:5 000).

The present invention also provides a method for determining the quantity of neutralising antibodies to a pre-synaptic neuromuscular blocking substance in a sample which comprises the following steps:

(i) determining the minimum voltage $V_{msm}$ needed to induce the contraction of smooth muscle tissue, said smooth muscle tissue being linked to an electrical stimulator through an electrically conducting liquid;

(ii) adding a mixture of the sample to be tested containing the neutralising antibodies to the pre-synaptic neuromuscular blocking substance and a determined quantity of said pre-synaptic neuromuscular blocking substance, said mixture having been pre-incubated at a temperature from 0 to 45° C. for a period from about 15 to about 120 minutes;

(iii) electrically stimulating, at a voltage at least equal to $V_{msm}$, the smooth muscle tissue at certain time intervals;

(iv) comparing the effect induced by the mixture to the effect induced by the determined quantity of said pre-synaptic neuromuscular blocking substance and thereby determining the quantity of neutralising antibodies to the pre-synaptic neuromuscular blocking substance in the sample.

All the variants indicated previously for the method for determining the quantity of a pre-synaptic neuromuscular blocking substance in a sample are applicable mutatis mutandis to the invention method for determining the quantity of neutralising antibodies to a pre-synaptic neuromuscular blocking substance in a sample.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented to illustrate the above and must in no case be considered as a limit to the scope of the invention.

EXAMPLES

In the following Examples, 1 Speywood or Dysport unit or 1 U corresponds to the median intraperitoneal $LD_{50}$ dose of botulinum toxin in mice.

Examples 1 to 3 are aimed at determining the quantity of a pre-synaptic neuromuscular blocking substance in a sample whereas Example 4 is aimed at determining the selectivity of such a substance with respect to smooth or striated muscles.

Example 1

Botulinum Toxin Containing Sample

Striated Muscle System

Materials Used
a) Buffer Solutions Used:
The modified Ringers buffer identified hereafter as "Liley's Ringers buffer" is prepared by diluting the following in water:

| | |
|---|---|
| NaCl | 138.8 mM |
| KCl | 4 mM |
| $NaHCO_3$ | 12 mM |
| $KH_2PO_4$ | 1 mM |
| $MgCl_2$ | 1 mM |
| $CaCl_2$ | 2 mM |

Immediately prior to use, glucose (11 mM) is added to the solution prepared previously and a gas mixture of 95% $O_2$ and 5% $CO_2$ is bubbled through the buffer solution to yield the Lillies Ringers buffer.

The Phosphate Buffered Saline solution (PBS) referred to hereafter is prepared by dissolution of a tablet supplied by Sigma which, when added to 200 ml of water, provides the following characteristics to the buffer:

| | |
|---|---|
| Phosphate buffer | 0.01 M |
| KCl | 0.0027 M |
| NaCl | 0.137 M |
| pH at 25 ° C. | 7.4 | b) Isolation of Tissue:

Wistar rats (approximate weight 275 g) are sacrificed by neck dislocation following $CO_2$ exposure (approximately 3 min to induce loss of consciousness). The rib cage is dissected from each animal, placed in Liley's Ringers buffer and transported to the experiment place (journey time: approximately 15 min). There the rib cage is separated into two sections by careful dissection along the spinal column. The tissues are stored in oxygenated buffer prior to carrying out the experimental procedures.

c) Determination of Minimum Voltage $V_{mst}$ Needed to Induce Muscle Contraction:

Each intercostal preparation (half rib cage) is placed into a Petri dish containing Lillies Ringers buffer. For each preparation, one intercostal nerve is carefully dissected to reveal approximately 1-2 mm of nerve bundle. Following dissection, the preparation can be revived in freshly oxygenated Liley's Ringers buffer for approximately 15-20 minutes before being returned to a Petri dish containing 10 ml of oxygenated Liley's Ringers buffer. The dissected intercostal nerve is then connected via a suction electrode to a stimulator (Grass Instruments Model S48), with a return contact electrode placed in the media. The minimum voltage $V_{mst}$ needed to induce muscle contraction is determined. If stimulation cannot be achieved below 10V, another nerve is dissected and the preparation revived prior to continuation.

Method for Determining the Quantity of Botulinum Toxin Contained in a Sample

The nerve is stimulated with a pulsed voltage (5-9V, 1 Hz), the voltage chosen always being 1 V above the threshold voltage $V_m$ required to achieve stimulation and muscle contraction. Video microscopy of the section is carried out with a Nikon SMZ800 stereomicroscope equipped with JVC TKC1481EG video camera connected to a combined TV/video recorder.

Dysport® (active principle: botulinum toxin type A) is added in PBS directly above the intercostal preparation (slightly submerged within 10 ml of buffer). For the 50 Speywood or Dysport units (U) per ml dose, 500 U of toxin is added to the culture dish (10 ml buffer) to yield a final concentration of 50 U/ml. For the 10 U/ml dose, 100 U is added to the culture dish to yield a final concentration of 10 U/ml. For the 1 U/ml dose, 10 U is added to the culture dish yielding a final concentration of 1 U/ml. For the placebo (which has the same composition as Dysport®, except that botulinum toxin is absent), the full contents of the vial (in 0.2 ml PBS) is added to the culture dish.

Data Analysis

The recorded video clips are converted to MPEG files. To assist with subsequent analysis, each movie is cut into 2-minute sections and these sections are slowed to ½ their initial speed using Adobe® Premiere® 5.1 software. Analysis is then performed by counting the number of twitches in a 10 s period (20 s on half speed clips) and averaging the number of twitches over this 10 s period to yield a value of twitch frequency. Contraction distance can also be measured by playing the movie with a superimposed scale bar (of arbitrary units—nominally a 6-7 point scale), the data being averaged to give the contraction distance over each 10 s period, or alternatively said distance is compared to the initial contraction distance.

The experiments are repeated a certain number of times (0 U/ml: n=5; 1 U/ml: n=5; 10 U/mi: n=4; 50 U/ml: n=4) and the results are averaged.

Results

Figure 1:
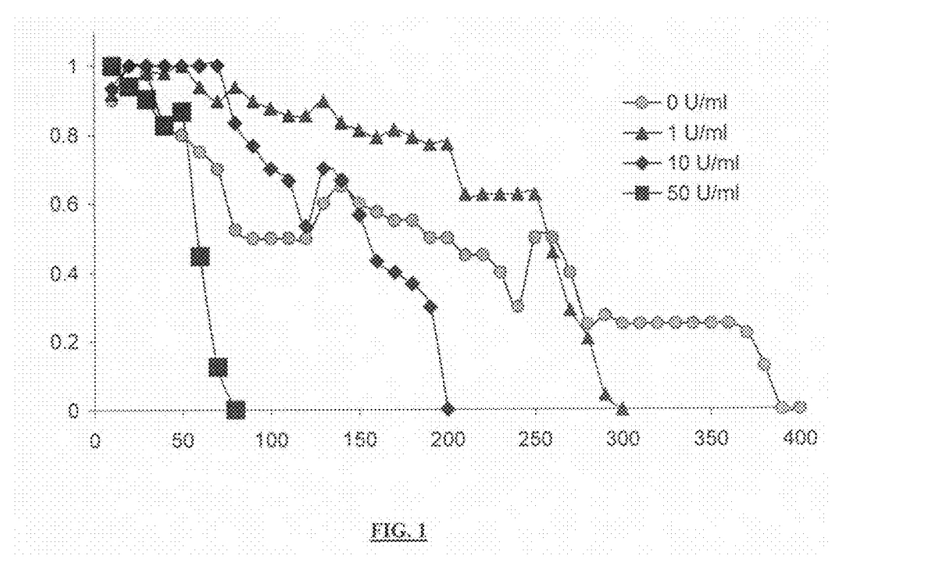
FIG. 1 shows the relative contraction distance of an intercostal rat preparation measured in function of time with varying Dysport® concentrations (0, 1, 10 and 50 U) according to the procedure described in Example 1 (striated muscle system). The X-axis shows Time (s), while the Y-axis shows Distance (normalised to contraction initial size).

From FIG. 1 one will see that the relative contraction distance (i.e. the contraction distance in the presence of toxin divided by the contraction distance in the absence of toxin) is reduced more or less quickly as a function of the Dysport® concentration.

Figure 2:
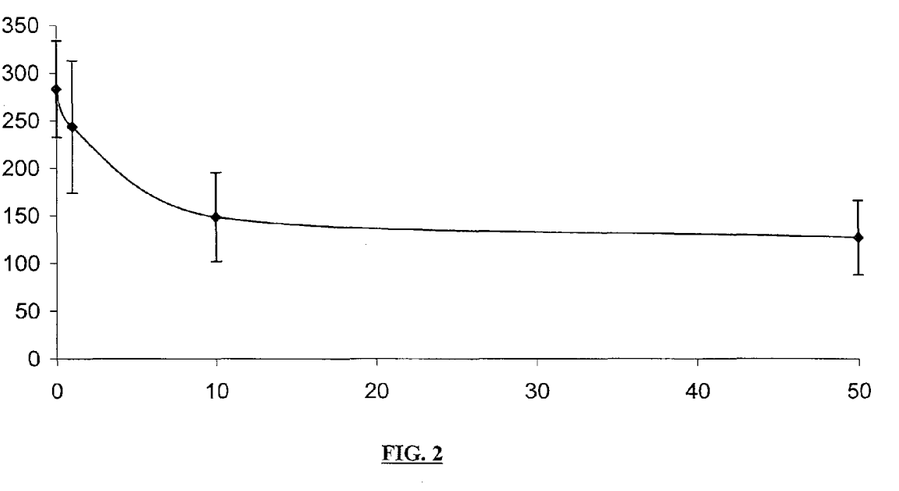
FIG. 2 shows the lifetime of an intercostal rat preparation measured from contraction distance with varying Dysport® concentrations (0, 1, 10 and 50 U) according to the procedure described in Example 1 (striated muscle system). The data shown are means±sem, n=4-5). "Sem" is standard error of the mean. The X-axis shows Dysport Concentration Time (LD50 Units/ml), while the Y-axis shows Time (s).

As can also be seen from FIG. 2 which shows results regarding the distance twitch lifetime (i.e. the time needed from the moment the toxin is added until the point when the contraction distance becomes zero), a dose-dependant reduction in the muscle contraction distance as a function of the Dysport® concentration can be observed.

Figure 3:
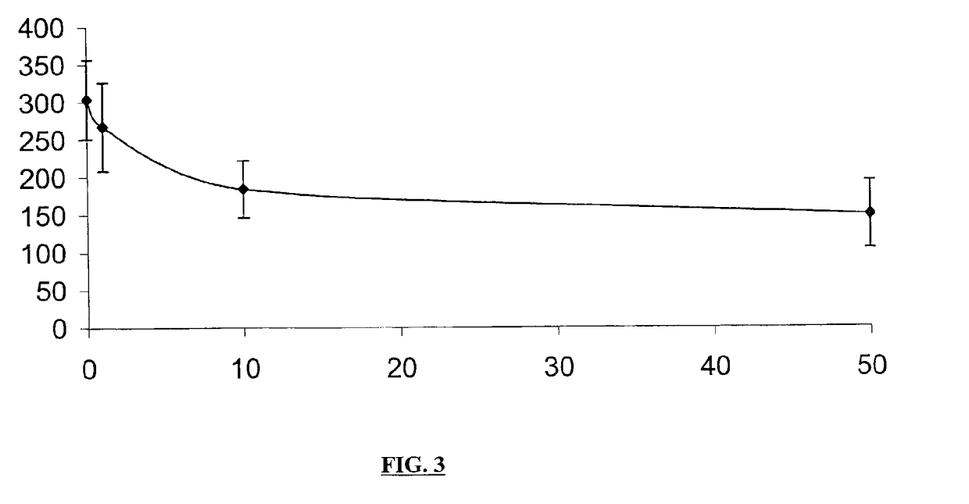
FIG. 3 represents the lifetime of an intercostal rat preparation measured from twitch frequency with varying Dysport® concentrations (0, 1, 10 and 50 U) according to the procedure described in Example 1 (striated muscle system). The data shown are means±sem, n=4-5). The X-axis shows Dysport Concentration Time (LD50 Units/ml), while the Y-axis shows Time (s).

The twitch frequency lifetime (i.e. the time needed from the moment the toxin is added until the point when the twitch frequency becomes zero) is also reduced by Dysport® in a dose-dependant manner as is shown in FIG. 3.

Example 2

α-Bungarotoxin Containing Sample

Using same procedure as described for Example 1, striated muscle system, α-bungarotoxin instead of Dysport® is tested at the concentration of 21 μM (n=3). The mean twitch lifetime of the α-bungarotoxin preparation is 225 s (±sem 93, n=3) and 238 s (±sem 93, n=3), measured from contraction distance and twitch frequency respectively.

Example 3

Extended Life System

Striated Muscle System

Material Preparation a) Buffer Solutions Used:

The modified Ringers buffer or "Liley's Ringers buffer" used in this Example is the same as for Example 1.

Figure 4:
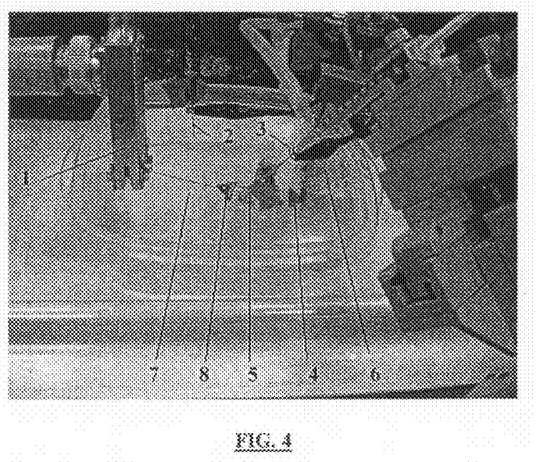
FIG. 4 shows a 2-rib tissue section attached to the force displacement transducer in a static bath setup. The meaning of the figures are the following:
1=Force displacement transducer
2=Electrode
3=Suction electrode
4=Fixed attachment
5=Staple
6=Gas disperser
7=Suture material
8=Free attachment

The Gelatine Phosphate Buffer (GPB) used in this Example is prepared by diluting the following in 1 liter of water:

| | |
|---|---|
| Gelatin | 2 g |
| $NaHPO_4$, 2 $H_2O$ | 10 g | b) Isolation of the Tissue:

Male Wistar rats (approximately 230-300 g) are sacrificed by neck dislocation following $CO_2$ exposure (approximately 3 minutes to induce loss of consciousness). The rib cage is dissected from the animal, placed in Liley's Ringers buffer and transported to the experiment place (journey time: approximately 20 minutes). There the rib cage is separated into two sections by careful dissection along the spinal column and sternum. The two halves of the rib cage are stored in approximately 300 ml of continually oxygenated Liley's Ringers buffer for at least 30 minutes prior to experimental procedures.

c) Determination of minimum voltage $V_m$ needed to induce muscle contractions:

One half of the rib cage is placed in a Petri dish containing approximately 10 ml of Liley's Ringers buffer and an intercostal nerve is carefully dissected to reveal approximately 1-2 mm of nerve bundle. This nerve is then connected via a suction electrode to a stimulator (Grass Instruments Model S48) with a return electrode placed in the media. The minimum voltage $V_m$ needed to induce muscle contraction is determined. If stimulation cannot be achieved below 10 V (1 Hz, 200 μsec duration), another nerve is dissected. The 2-rib section containing the dissected nerve is dissected from the half rib cage, ensuring as much excess muscle tissue as possible remains either side of the 2 ribs for later attachment to the force displacement transducer.

d) Attachment to the Force Displacement Transducer:

Three metal staples are attached to the non-stimulated muscle tissue on either side of the two ribs. One side of the 2-rib section is attached to the fixed foot via the three staples whilst the other side was affixed to the free foot. The fixed foot is clamped securely in place while the free foot was attached to the force displacement transducer (Grass Instruments Model FT03) via approximately 4 cm of cotton thread. The fixed tissue is immersed in approximately 500 ml Liley's Ringers buffer, and a return electrode placed within the buffer. The dissected intercostal nerve was connected via a suction electrode to the stimulator. This system is shown in FIG. 4.

Method for Determining the Quantity of Botulinum Toxin Contained in a Sample

The 2-rib tissue sections are stimulated for approximately 90 minutes at 15 V, 200 μsec duration using train pulse stimulation (1 pulse/second for the first 5 seconds of every 30 second period).

The required concentration of toxin is reconstituted in GPB immediately prior to application. The toxin delivery is via one of two methods:

A) Direct application—The 2-rib section is exposed to the air/liquid interface by removal of some of the buffer within the tissue bath. Using a Hamilton syringe, the toxin is applied directly onto the exposed tissue in a drop wise fashion, coating the muscle in the toxin solution. The tissue is left exposed for a further 15 minutes to enable uptake of the toxin before covering that with the original Ringers buffer. If necessary, any dislodged, dissected nerves are reconnected to the suction electrode.

B) Immersion—Using a Hamilton syringe, the toxin is applied directly into the tissue bath in close proximity to (but not directly onto) the 2-rib section.

Twitch force readings recorded from the force displacement transducer are first amplified throughout a Grass Instruments AC/DC strain gage amplifier (Model P122) and signals are then recorded using Grass PolyVIEW™ software.

Data Analysis

From the traces recorded, the time taken for the initial maximal twitch force measurement (after addition of toxin/placebo) to decrease by a certain percentage was measured. The experiments are repeated a certain number of times (direct application method: placebo: n=4; 500 U: n=8; 1000 U: n=5; 1500 U: n=11; immersion method: placebo: n=3; 3 U/ml: n=5; 6 U/ml: n=2, 12 U/ml: n=2). Due to the long life span of the tissue when exposed to placebo and low levels of toxin, values illustrated at the 90% reduction in twitch force are estimated results based on the extrapolation of the data assuming a constant rate of decline.

Results

A) Direct Application Method

Figure 5:
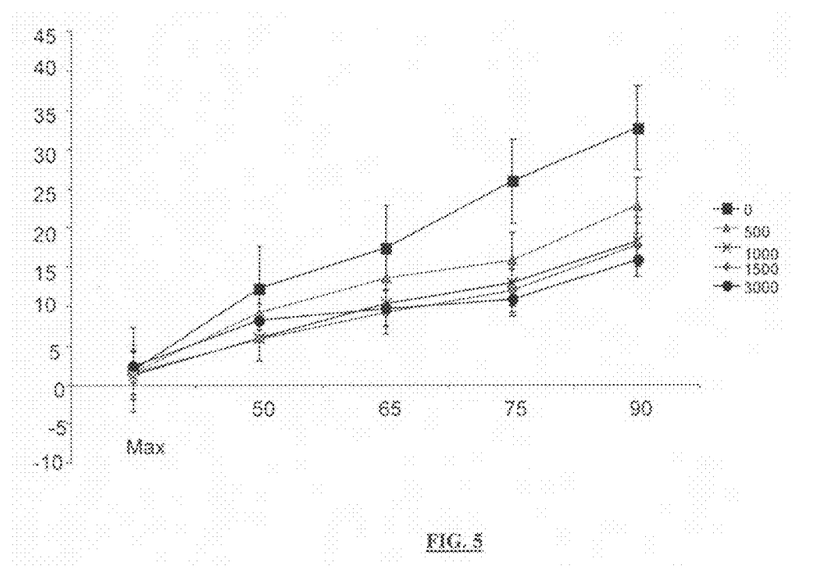
FIG. 5 shows the time taken (hours) for the maximal twitch force measurements of 2-rib sections exposed to either placebo or 500, 1000, 1500 or 3000 U of toxin using the direct application method of Example 3 in the static system of the striated muscle system (the following numbers of experiments n apply: placebo: n=4; 500 U: n=8; 1000 U: n=5; 1500 U: n=11). Error bars illustrate ±S.E.M. The X-axis shows % Reduction in Maximal Twitch Force, while the Y-axis shows Time (Hours).

Over time, a gradual reduction in twitch force measurements are recorded in all samples, including after the addition of placebo as seen in FIG. 5. Following placebo exposure, a 50% reduction in maximal twitch force is observed after over approximately 12 hours. In comparison, twitch force is reduced more rapidly in those tissue samples exposed to 1500 U of toxin, with a 50% reduction being reached after approximately 5 hours.

B) Immersion Method

Figure 6:
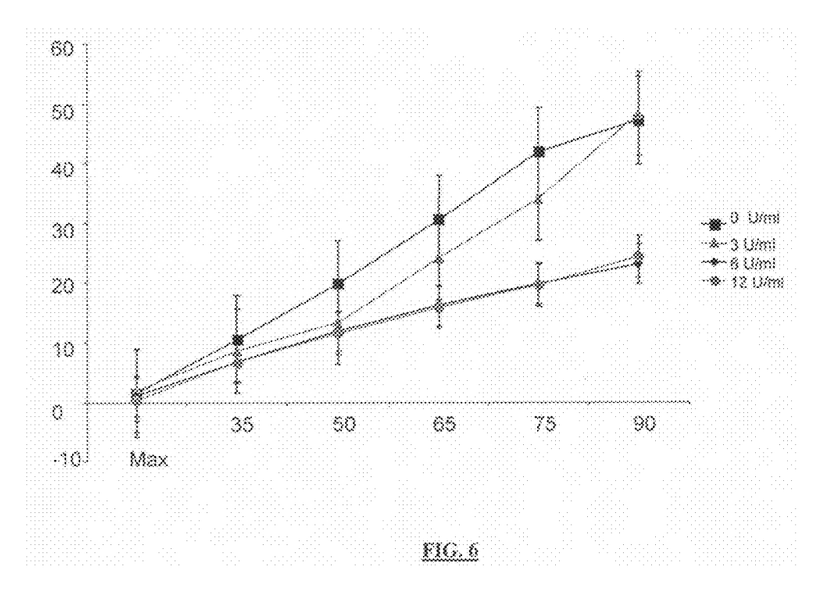
FIG. 6 shows the time taken (hours) for the maximal twitch force measurements of 2-rib sections exposed to either placebo or 3, 6 or 12 U/ml of toxin using the immersion method of Example 3 in the static system of the striated muscle system (the following numbers of experiments n apply: placebo: n=3; 3 U/ml: n=5; 6 U/ml: n=2; 12 U/ml: n=2). Error bars illustrate ±S.E.M. The X-axis shows % Reduction in Maximal Twitch Force, while the Y-axis shows Time (Hours).

Reductions in twitch force measurements were recorded after the addition of placebo with a 50% reduction in maximal twitch force observed after approximately 20 hours as seen in FIG. 6. Immersing the tissue in a 3 unit/ml solution of toxin further increased the rate of twitch force reduction with a 50% reduction in twitch force reached after 13 hours of stimulation. At higher toxin concentrations, a dose dependent response is still evident.

As one can see, a repeatable dose dependent toxin-induced suppression of muscle contraction is observed using both the direct application and immersion methods of toxin delivery.

Example 4

Extended Life System

Striated Muscle System

The system using a striated muscle is identical to that of Example 3, except that a pig rib cage muscle with an intercostals nerve is used instead of the rat rib cage muscle.

Smooth Muscle System

The system using a smooth muscle tissue sample is analogous to that described previously for the striated muscle (rat rib cage muscle) preparation, except that a rat bladder muscle preparation is used instead of the rat rib cage muscle preparation and Krebs-Henseleit buffer is used instead of Lillies Ringers buffer.

Krebs-Henseleit buffer is prepared by diluting the following in water:

| Component | Concentration (g/l) |
|---|---|
| D-glucose | 2.1 |
| Magnesium sulphate ($MgSO_4$) | 0.29 |
| Monobasic potassium phosphate ($KH_2PO_4$) | 0.16 |
| Potassium chloride (NaCl) | 0.35 |
| Sodium chloride (NaCl) | 6.9 |
| Calcium chloride ($CaCl_2$) | 0.282 |
| Sodium bicarbonate $NaHCO_3$ | 2.1 |

The preparation of the rat bladder for the experiment is carried out as follows:

1) The detrusor muscle is dissected from the neck of the bladder in strips (ca. 2 mm×2 mm×10 mm); and
2) The tissue is mounted in individual 10 ml tissue baths fitted with tissue electrodes and filled with Krebs-Henselett buffer.

Figure 7:
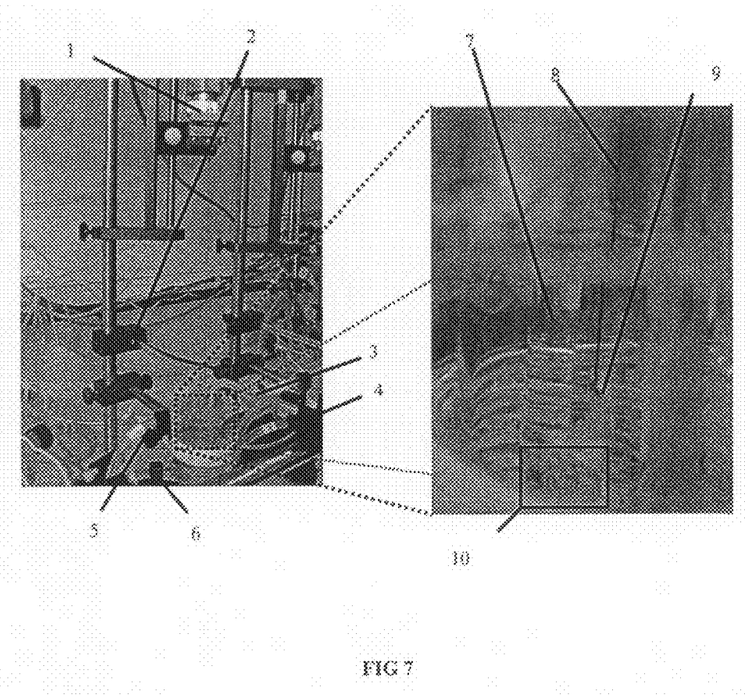
FIG. 7 shows a bladder tissue section attached to the force displacement transducer in a tissue organ bath setup. The meaning of the figures are the following:
1=Force transducer
2=Glass hook clamp
3=Electrode
4=Electrode clamp
5=Overflow
6=Jacket-in
7=Glass hook
8=Suture
9=Rat bladder strip
10=Electrode coil

Material Preparation a) Isolation of the Tissue:

Male Wistar rats (approximately 230-300 g) are sacrificed by neck dislocation following $CO_2$ exposure (approximately 3 minutes to induce loss of consciousness). The bladder is dissected from the animal, placed in Krebs Henseleit buffer and transported to the experiment place (journey time:

approximately 20 minutes). There the bladder is opened out and separated into two transverse strips.

b) Attachment to the Force Displacement Transducer:

30 cm of surgical suture is attached to one end of the tissue strip, and secured with three knots. A 15 cm length of surgical suture is threaded half way through the tissue, leaving 7.5 cm either side. A knot is then half-tied using each end of the suture; the knot is pulled tight over the tissue and a glass hook, before two further knots are tied to secure the attachment. Once each strip is attached to the glass hook, the hook is placed into a tissue bath containing 37° C. Krebs buffer gassed with 95% $O_2$/5% $CO_2$. Once all the bladder strips are prepared, the tissues are hooked up to the force transducer in the same order. Three knots are tied around a metal S-hook using the 30 cm length of suture. The S-hook is then attached to the force transducer. The PolyVIEW™ recording software is started at this point. Each piece of tissue is then pre-tensioned by quickly raising the force transducer until the equivalent of a 10 g force (5 V) is measured on the P122 strain gauge amplifier (Grass, Astro Med) digital display. The tissue strips undergo an exponential stretch-relaxation observed as a reduction in force measured. The relaxation is allowed to occur under non-stimulation conditions for 1 hour prior to experimental stimulation of the tissue. This system is shown in FIG. 7.

Method for Determining the Quantity of Botulinum Toxin Contained in a Sample

The smooth muscle tissue sections are stimulated for approximately 90 minutes at 20 V, 300 μsec duration at 20 Hz using train pulse stimulation (1 train of pulses for the first 5 seconds of every 60 second period).

The required concentration of toxin is reconstituted in GPB immediately prior to application. Direct application method—The smooth muscle section is exposed to the air/liquid interface by removal of some of the buffer within the tissue bath. The toxin is applied directly onto the exposed tissue in a drop wise fashion, coating the muscle in the toxin solution. The tissue is left exposed for a further 15 minutes to enable uptake of the toxin before covering that with the original Krebs Henseleit buffer.

Contraction force readings recorded from the force displacement transducer are first amplified throughout a Grass Instruments AC/DC strain gage amplifier (Model P122) and signals are then recorded using Grass PolyVIEW™ software.

Data Analysis

From the traces recorded, the time taken for the initial maximal twitch force measurement (after addition of toxin/control) to decrease by a certain percentage is measured. The experiments are repeated a certain number of times (control n=7; 1000 U: n=1; 500 U: n=4; 250 U: n=6, 100 U: n=12).

Results

Figure 8:
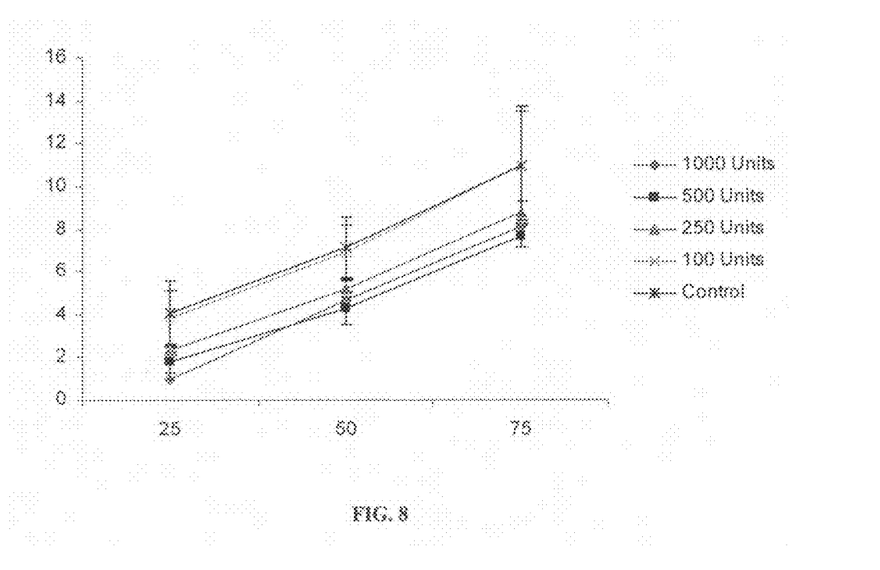
FIG. 8 shows the time taken (hours) for the maximal contraction force measurements of bladder tissue sections exposed to either buffer control or 100, 250 or 500 or 1000 U of toxin using the direct application method of Example 3 in the tissue organ bath of the smooth muscle system (the following numbers of experiments n apply: control: n=7; 100 U: n=12; 250 U: n=6; 500 U: n=4; 1000 U: n=1). Error bars illustrate ±S.D. "S.D." is Standard Deviation. The X-axis shows % Reduction in Maximal Twitch Force, while the Y-axis shows Time (Hours).

Over time, a gradual reduction in contraction force measurements are recorded in all samples, including after the addition of GPB (control) as seen in FIG. 8. Following control exposure, a 75% reduction in maximal contraction force is observed after over approximately 11 hours. In comparison, contraction force is reduced more rapidly in those tissue samples exposed to 500 U of toxin, with a 75% reduction being reached after approximately 7 hours.

Example 5

Selectivity Determination

The systems of Examples 4 are used for determining selectivity of pre-synaptic neuromuscular blocking substances, namely biologically active botulinum toxin fragments.

The same pre-determined nanomolar quantity of biologically active botulinum toxin fragments is used in each of the striated muscle and smooth muscle systems instead of an unknown amount.

The ratios of the times needed to get a certain reduction in twitch force (e.g. the times to get a reduction of 50%) in smooth muscles and in striated muscles can be used as indicators of the selectivity of said biologically active botulinum toxin fragments with respect to smooth or striated muscles.

The invention claimed is:

1. A method for determining the selectivity of a pre-synaptic neuromuscular blocking substance comprising the following steps:
   (a) determining the minimum voltage $V_{mst}$ needed to induce the contraction of a striated muscle tissue, said striated muscle tissue being connected to an electrical stimulator through a motor nerve;
   (b) adding to the system of step (a) a pre-determined quantity of a pre-synaptic neuromuscular blocking substance;
   (c) electrically stimulating, at a voltage at least equal to $V_{mst}$, the muscle tissue by train pulse stimulation, thereby extending life span of the muscle tissue and carrying out the stimulation over a period of at least 1 hour to increase the sensitivity of the method;
   (d) measuring the effect induced by the pre-determined quantity of a pre-synaptic neuromuscular blocking substance on the striated muscle tissue, said effect being selected from (i) time to paralysis of said striated muscle tissue, (ii) variation in the contraction rate of said striated muscle tissue, (iii) variation in the contraction distance of said striated muscle tissue, (iv) variation in the force of contraction of said striated muscle tissue, and (v) variation in the end plate potential or the miniature end plate potential of said striated muscle tissue;
   (e) determining the minimum voltage $V_{msm}$ needed to induce the contraction of a smooth muscle tissue, said smooth muscle tissue being linked to an electrical stimulator through an electrically conducting liquid;
   (f) adding to the system of step (e) the same pre-determined quantity of the same pre-synaptic neuromuscular blocking substance as for step (b);
   (g) electrically stimulating, at a voltage at least equal to $V_{msm}$, the muscle tissue by train pulse stimulation, thereby extending life span of the muscle tissue and carrying out the stimulation over a period of at least 1 hour to increase the sensitivity of the method;
   (h) measuring the effect induced by said pre-determined quantity of the pre-synaptic neuromuscular blocking substance on the smooth muscle tissue, said effect being selected from (i) time to paralysis of said smooth muscle tissue, (ii) variation in the contraction rate of said smooth muscle tissue, (iii) variation in the contraction distance of said smooth muscle tissue, (iv) variation in the force of contraction of the smooth muscle tissue, and (v) variation in the end plate potential or the miniature end plate potential of said smooth muscle tissue; and
   (i) calculating the quotient of the result obtained in step (h) by the result obtained in step (d), wherein, the higher above 1 said quotient is, the more selective for smooth muscle the pre-synaptic neuromuscular blocking substance is; or, conversely, calculating the quotient of the result obtained after step (d) by the result obtained after step (h), wherein, the higher above 1 said quotient is, the more selective for striated muscle the pre-synaptic neuromuscular blocking substance is.

2. The method of claim 1, wherein said striated muscle tissue and said smooth muscle tissue are derived from the same animal species.

3. The method of claim 1, wherein said muscle tissue is immersed in a buffer.

4. The method of claim 3, wherein said buffer is a physiological buffer.

5. The method of claim 3, wherein said buffer comprises an energy source.

6. The method of claim 5, wherein said energy source is an ATP energy source.

7. The method according to claim 3, wherein said buffer is oxygenated.

8. The method according to claim 7, wherein said buffer is an oxygenated physiological buffer containing glucose.

9. The method of claim 1, wherein said pre-synaptic neuromuscular blocking substance is a botulinum toxin.

10. The method of claim 9, wherein said botulinum toxin is selected from botulinum toxin type A, botulinum toxin type B and botulinum toxin type F.

11. The method of claim 9, wherein said botulinum toxin is selected from botulinum toxin type A and botulinum toxin type B.

12. The method of claim 11, wherein said botulinum toxin is botulinum toxin type A.

13. The method of claim 1, wherein said pre-synaptic neuromuscular blocking substance is a bungarotoxin.

14. The method of claim 13, in which the bungarotoxin is α-bungarotoxin.

* * * * *